(12) United States Patent
Schipper et al.

(10) Patent No.: US 8,867,704 B2
(45) Date of Patent: Oct. 21, 2014

(54) METHOD FOR X-RAY DIFFRACTOMETRY ANALYSIS AT DIFFERING WAVELENGTHS WITHOUT EXCHANGING THE X-RAY SOURCE

(75) Inventors: Rolf Schipper, Karlsruhe (DE); Joachim Lange, Hagenbach (DE)

(73) Assignee: Bruker AXS GmbH, Karlsruhe (DE)

( * ) Notice: Subject to any disclaimer, the term of this patent is extended or adjusted under 35 U.S.C. 154(b) by 398 days.

(21) Appl. No.: 13/137,699

(22) Filed: Sep. 6, 2011

(65) Prior Publication Data
US 2012/0106706 A1    May 3, 2012

(30) Foreign Application Priority Data
Oct. 27, 2010   (DE) .................. 10 2010 043 028

(51) Int. Cl.
*G01N 23/20*   (2006.01)
(52) U.S. Cl.
CPC ...... *G01N 23/20091* (2013.01); *G01N 2223/33* (2013.01); *G01N 2223/1016* (2013.01); *H01J 2235/081* (2013.01)
USPC .......................................................... 378/71
(58) Field of Classification Search
CPC .............................. G01N 23/20; G01N 23/207
USPC ..................................................... 378/70–90
See application file for complete search history.

(56) References Cited

U.S. PATENT DOCUMENTS

| | | | |
|---|---|---|---|
| 3,336,494 A | 8/1967 | Shinichi | |
| 3,743,841 A | 7/1973 | Herglotz | |
| 3,778,654 A | 12/1973 | Hueschen | |
| 3,836,808 A | 9/1974 | Friedel | |
| 5,148,462 A | 9/1992 | Spitsyn | |
| 5,491,738 A | 2/1996 | Blake | |
| 7,317,784 B2 | 1/2008 | Durst | |
| 2004/0066896 A1 | 4/2004 | Fujinawa | |
| 2007/0003012 A1* | 1/2007 | Taguchi et al. ................. | 378/71 |
| 2010/0092699 A1 | 4/2010 | Steinlage | |
| 2011/0317813 A1* | 12/2011 | Matsushita et al. ............. | 378/73 |

FOREIGN PATENT DOCUMENTS

| | | |
|---|---|---|
| CN | 101290852 | 10/2008 |
| DE | 195 36 917 | 4/1997 |
| EP | 0 062 380 | 10/1982 |

(Continued)

OTHER PUBLICATIONS

Sung-Dae Chun et al., "Property of a CZT Semiconductor Detector for Radionuclide Identification" Journal of Nuclear Science and Technology, Supplement 5, p. 421-424 Jun. 2008.

(Continued)

*Primary Examiner* — Courtney Thomas
(74) *Attorney, Agent, or Firm* — Paul Vincent

(57) ABSTRACT

A method for performing an X-ray diffractometry analysis of a crystalline and/or amorphous sample, by means of an optical X-ray apparatus having an X-ray source with an X-ray anode constructed from a mixed configuration of at least two metals is characterized in that an energy-dispersive semiconductor is used for acquiring detector events from the X-rays emanating from the sample, and that X-rays diffracted or scattered by the sample with different characteristic energy lines belonging to the metals of the mixed configuration of the X-ray anode used, are acquired simultaneously during an angle scan. With this method, X-ray diffractometry analysis with multiple characteristic energy lines are possible without any need for conversion or switchover.

14 Claims, 2 Drawing Sheets

(56) References Cited

FOREIGN PATENT DOCUMENTS

| | | |
|---|---|---|
| EP | 1 732 101 | 12/2006 |
| EP | 1 739 413 | 1/2007 |
| GB | 551 897 | 3/1943 |
| GB | 574 109 | 12/1945 |
| GB | 1 032 118 | 6/1966 |
| JP | 3257744 A | 11/1991 |
| JP | 5 135722 | 6/1993 |
| JP | 11 304728 | 11/1999 |

OTHER PUBLICATIONS

Asakura Shoten, "Practice of Powder X-ray Analysis, Second Edition", pp. 26-29, Jul. 10, 2009.

* cited by examiner

METHOD FOR X-RAY DIFFRACTOMETRY ANALYSIS AT DIFFERING WAVELENGTHS WITHOUT EXCHANGING THE X-RAY SOURCE

This application claims Paris convention priority of DE 10 2010 043 028.5 filed Oct. 27, 2010, the entire disclosure of which is hereby incorporated by reference.

BACKGROUND OF THE INVENTION

The invention relates to a method for performing an X-ray diffractometry analysis of a crystalline and/or amorphous sample, by means of an optical X-ray apparatus with an X-ray source that has an X-ray anode constructed from a mixed configuration of at least two metals.

Such an X-ray anode is known from DE 195 36 917 A1

In X-ray diffractometry (XRD), discrete X-ray energy (usually K-alpha radiation of the anode material) is used to generate interferences (reflexes) on three-dimensional periodic structures at an atomic scale (crystals) according to Bragg's Law. The angle and intensity of the reflexes contain important information about the atomic and micro structure of the substances to be analyzed.

Therein, certain material characteristics of the crystal samples can be analyzed and determined by special X-ray line energies. These include not only absorption, anomalous dispersion, measurable angular range, disturbing or useful X-ray fluorescence signals of the sample, but also additional wavelength-dependent effects. Metals typically used in XRD X-rays are Cu (1.54184 angstrom), Co (1.7906 angstrom), Cr (2.29100 angstrom), Fe (1.93736 angstrom) and Mo (0.71073 angstrom) and for example, Ag (rel. high energies) is also sometimes used.

Typical applications/analyses for the various characteristic energies: Cu radiation is suitable for most XRD analyses, while Mo radiation is preferred, for example, for the analysis of steels and metallic alloys in the range Ti (A=22) to around Zn (A=30). Co radiation is often used in conjunction with samples containing Fe as it is often not possible to avoid disturbing iron fluorescence radiation in any other way. Fe radiation is also used, for example, for samples containing Fe and for minerals where Co or Cr radiation cannot be used. Cr radiation is suitable for complex organic substances and stress measurement of steel. Characteristic W radiation can only be excited when electron energies are very high. W tubes are therefore used if radiation continuity is more important than individual lines and they are not suitable for XRD measurements.

Until now, the aim has always been to use X-ray anodes for XRD which are made of pure element metals because, without the ability to discriminate between energies, metal impurities in the anode material can result in disturbing reflexes in the diffraction image and misinterpretation of the measurement result. For cost reasons, a scintillation counter is often used which, although extremely sensitive and able to detect individual photons, it is not able to resolve photon energies that are close together in the spectrum.

The X-ray tube on existing X-ray diffractometers is sometimes replaced in order to exchange the anode material and to prepare the diffractometer for measuring other samples. This conversion can be very time-consuming, since, as in most cases, the entire equipment has to be readjusted to the primary beam (including the detector electronics) that is directed onto the sample.

Many experiments have been carried out in the past with anodes made of alloys or other metal compounds.

In 1963, British patent GB1 032 118 A disclosed a method for manufacturing metal alloys with molybdenum or tungsten.

U.S. Pat. No. 3,778,654 A describes an X-ray anode made of a W—Mo alloy (for mammography). Mo is particularly suitable for the analysis of the affected boneless tissue. The strain placed on the anode by electron bombardment is considerable. The alloy of Mo with W in a particular proportion offers considerable advantages over anodes with pure Mo (robustness, lower therm. fatigue etc.).

U.S. Pat. No. 3,836,808 A, describes a rotating anode which is made of 75% Mo and up to 25% of a metal with an atomic number between 39 and 46 (Y, Zr, Nb, Mo, Tc, Ru, Rh, Pd). The patent describes how the effectiveness of anodes made of pure molybdenum decreases due to roughening. The alloys described are designed to minimize or delay roughening.

As long ago as 1943, anodes for X-ray apparatus for industrial/medical applications were described in British patent GB 551,897 A. The anodes described consist of a combination of a finely distributed phase of tungsten and a continuous phase of Cu, Ag, or Au. Such anodes exhibit a high X-ray output combined with a high resistance to electron bombardment and good thermal conductivity. They can also be manufactured by compression and sintering processes.

EP 0 062 380 describes a coated X-ray anode, consisting of W, Mo and a W—Mo alloy, as well as a method for manufacturing same. The patent describes the conditions (temp. etc.) under which certain layers can be applied by vacuum coating from the gas phase. The substrate is described as a combination of Mo, Ti, Zr and C. One of the layers is described as a combination of W and a W alloy containing portions of Rh, Ta, Os, Ir, Pt and similar elements. One layer is described that contains Re.

The primary objective of the development was to create durable, robust anodes and/or alloys, wherein only one specific energy line was used for the X-ray diffractometry itself.

U.S. Pat. No. 7,317,783 B2 discloses an X-ray anode that is composed of different metals in several zones. The electron beam can be aimed in such a way that only one zone is bombarded. In this way, the sample can be analyzed using individual energy lines of different pure metals. This invention is also intended to excite individual energy lines while eliminating the time-consuming conversion required to exchange the anode material.

DE 195 36 917 A1 discloses an X-ray anode for X-ray fluorescence (XRF) analysis. To ensure optimum excitation of XRF samples, several X-ray lines in the spectrum are desirable. An X-ray anode comprising a combination of several metals is the subject of the invention described in the publication. It enables multi-element analyses for XRF analyses. It is pointed out that basically all stable metal mixtures/alloys can be used, although Mo and W, in particular, are advantageous. Such an anode is advantageous for X-ray fluorescence analysis but unsuitable for X-ray diffractometers with scintillation counters.

In recent years, the use of energy-dispersive semi-conductor detectors has increased at an ever increasing rate; the gradual reduction in price being one of the reasons for this. These detectors can very precisely assign the measured photons to an energy in the X-ray spectrum. Even low-cost detectors achieve resolutions in the range of a few hundred electron volts. This makes it possible to separate and individually evaluate typical characteristic energy lines (see list above) in the spectrum. Even K-alpha and K-beta X-ray lines of an element (in the anode) can be separated from each other. Information is then obtained about the sample by means of a measurement (angle scan), which is derived from two different energies. Simultaneous measurement with 2 wavelengths (K-alpha & K-beta of the anode material) is already possible with the use of a suitable detector (XFlash from Bruker nano).

The object of this invention is therefore to present a method by which X-ray diffractometry analyses with multiple characteristic energy lines are possible without any need for conversion or switchover.

SUMMARY OF THE INVENTION

This object is solved inventively and surprisingly simply and effectively in that an energy-dispersion semi-conductor detector for acquiring detector events from the X-rays emanating from the sample is used, and that X-rays diffracted or scattered by the sample with different characteristic energy lines belonging to the metals of the mixed configuration of the X-ray anode used are acquired simultaneously during an angle scan.

If X-ray tubes with mixed anodes are used in conjunction with a suitable energy-dispersive detector with high resolution and suitable evaluation electronics (for example, XFlash from Bruker nano, Berlin) on a standard diffractometer (e.g. D2 Phaser), simultaneous measurements with many different energies are possible. The XFlash detector can separately count the detector events in up to 8 windows in the spectrum, which can be set arbitrarily, in counters assigned to each of the windows. For example, if a mixed anode of Cu, Co, Mo is used, the energies Cu—K-alpha, Cu—K-beta, Co—K-alpha, Co—K-beta, Mo—K-alpha, Mo—K-beta are simultaneously available. Windows can then be placed on the energy lines in the spectrum Cu—K-alpha, Cu—K-beta, Co—K-alpha, Co—K-beta, Mo—K-alpha, Mo—K-beta. When a single angle scan is started, the assigned counters simultaneously count the photons of the existing energies and assign them to the angle of the detector. The result is 6 diffractograms, which were simultaneously acquired during a single angle scan at different energies. The individual mixture ratios, in this example Cu/Co/Mo, can be selected such that the K-alpha energy lines are approximately equal in intensity.

The advantages of this method are as follows: Conversion of the system from Cu to Co and then to Mo (as an example) is no longer necessary, neither are readjustments or realignments to the primary X-rays from the Cu, Co and Mo tubes. This results in considerable time savings. The concurrent existence of several different energies considerably extends the applicability of the diffractometer while keeping operation simple. The operator can select the data set(s) that he or she requires for the evaluation. Furthermore, cost savings can be expected because only 1 X-ray tube is required.

In an especially preferred variant of the inventive method, the characteristic energy lines of both the $K\alpha$ and the $K\beta$ energies of several or of all the metals that are present in the mixed configuration are acquired simultaneously during an angle scan.

In a further variant of the inventive method, the detector events to be acquired are counted in several ranges that can be freely defined in the energy spectrum by the user.

A further embodiment of the inventive method is characterized in that a separate diffractogram is created for each defined range.

In another advantageous variant of the inventive method, the mixture ratio of the metals in the X-ray anode is selected such that the intensity of its $K\alpha$ energy lines measured is equal or that the $K\alpha$ energy lines exhibit a different desired intensity ratio.

The scope of the invention also includes a device for performing the inventive method, comprising an optical X-ray apparatus suitable for X-ray diffractometry, wherein an energy-dispersive semi-conductor detector is provided as the detector and the X-ray anode is constructed from a mixed configuration of at least two metals with different characteristic energy lines.

A further embodiment of the device is characterized in that the mixed configuration of the at least two metals is an alloy.

As an alternative, an embodiment is advantageous in which the mixed configuration of the at least two metals comprises a sintered powder mixture.

Yet another alternative is an embodiment of the device in which the mixed configuration comprises an alternating configuration of strips of at least two pure metals.

An embodiment of the inventive device is also considered advantageous in which the mixed configuration of the X-ray anode contains Cu and Co.

In a further variant of this embodiment of the inventive device, the mixed configuration of the X-ray anode also contains Cr and/or Fe.

An embodiment is also advantageous in which the mixed configuration of the X-ray anode also contains molybdenum.

Especially preferred is an embodiment of the inventive device which is characterized in that the energy-dispersive semi-conductor detector is a single- or multi-dimensional array detector.

DESCRIPTION OF THE PREFERRED EMBODIMENT

Figure 1:
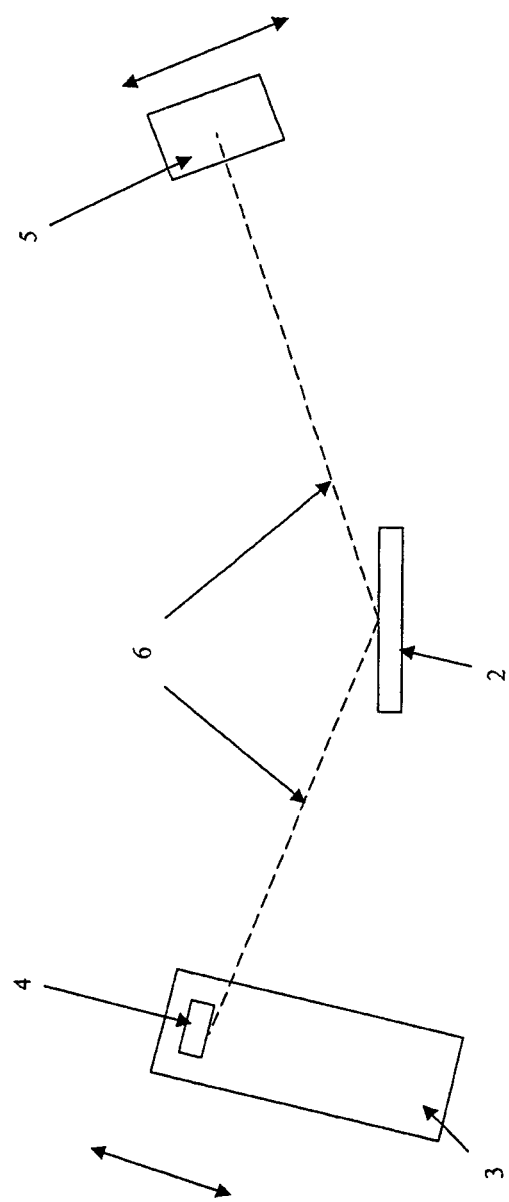
FIG. 1 a schematic representation of a device for performing the inventive method.

FIG. 1 shows a schematic representation of a device 1 suitable for performing the method. The device 1 comprises an X-ray source 3, which has an X-ray anode 4. The X-ray anode 4 is an anode comprising a mixed configuration of several metals. This can be an alloy, a sintered powder mixture or a configuration of strips of different metals.

The X-ray beam 6 from the X-ray source 3 strikes the sample 2. This might be a crystalline or an amorphous powder sample or even a silicon wafer, to name but a few examples.

The diffracted X-ray beam 6 passes from the sample 2 to the detector 5, which can be swept through a certain angular range so that it can be adapted to the diffraction angle. During an angle scan, the detector is moved through a predetermined angular range and the detector events are acquired in dependence on the angle. Therein, the diffraction reflexes are acquired in their discrete angles.

Figure 2:
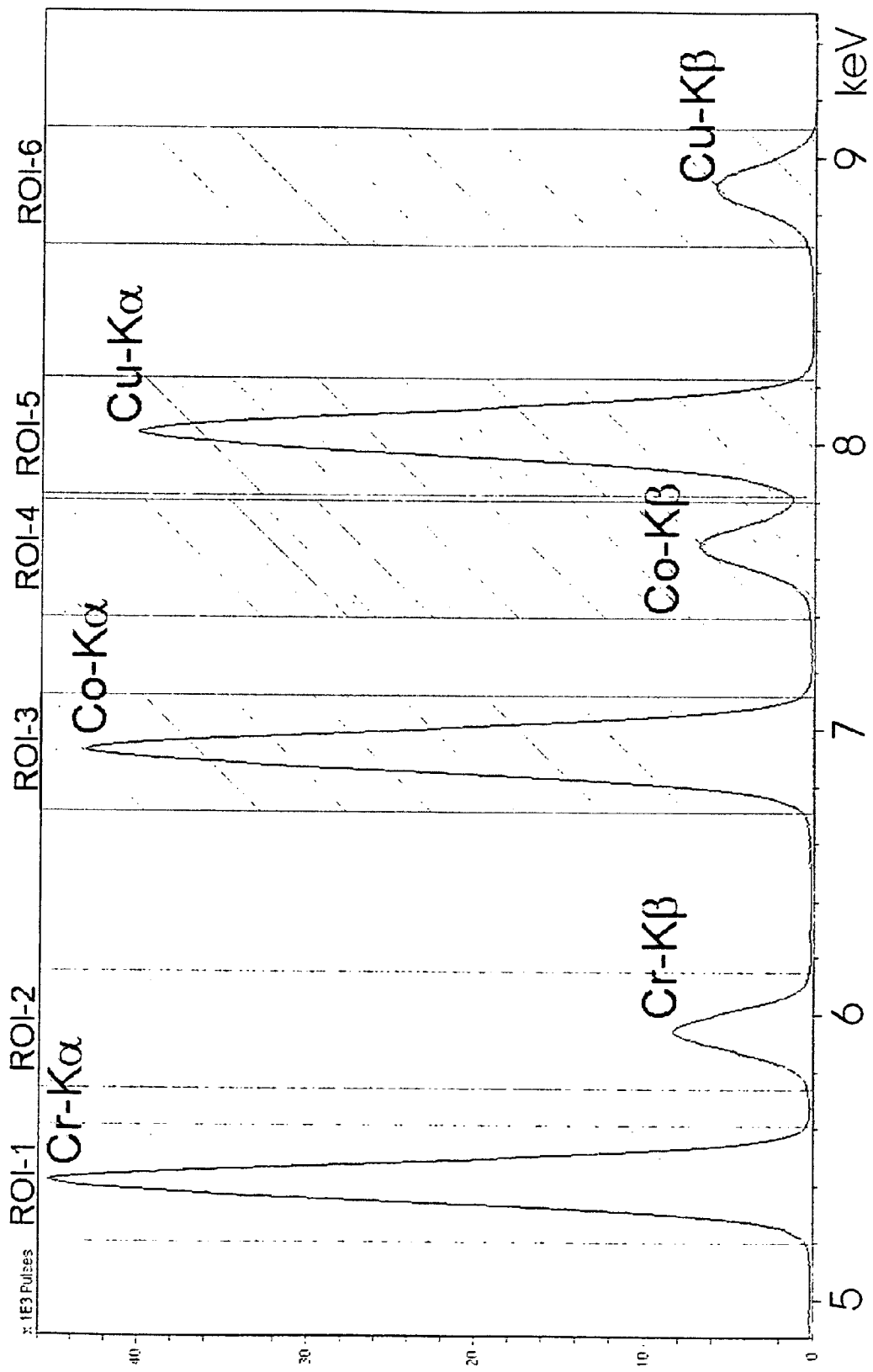
FIG. 2 an energy spectrum of the characteristic K-alpha and K-beta lines of Cu, Co and Cr.

FIG. 2 shows an energy spectrum that was acquired by the inventive method. It shows the characteristic K-alpha and K-beta lines of copper (Cu), cobalt (Co) and chromium (Cr). The energy windows ROI (region of interest) 1 to ROI 6 are set in such a way that the lines (useful beam) are almost completely covered without the ROIs overlapping.

LIST OF REFERENCE SYMBOLS

1 Device
2 Sample
3 X-ray source

4 X-ray anode
5 Detector
6 X-ray beam

We claim:

1. A method for performing an X-ray diffractometry analysis of a sample using an optical X-ray apparatus, the method comprising the steps of:
   a) preparing an X-ray source having an X-ray anode constructed from a mixed configuration of at least two metals, the mixed configuration of the at least two metals comprising a sintered powder mixture;
   b) preparing an energy-dispersive semi-conductor detector for acquiring counter events from the X-rays emanating from the sample;
   c) directing X-rays emanating from the X-ray source onto a crystalline and/or amorphous sample; and
   d) simultaneously acquiring, during an angle scan, X-rays diffracted or scattered by the sample with different characteristic energy lines belonging to the metals of the mixed configuration in the X-ray anode.

2. The method of claim 1, wherein the characteristic energy lines of both $K\alpha$ and the $K\beta$ energies of several or of all the metals that are present in the mixed configuration are acquired simultaneously during an angle scan.

3. The method of claim 1, wherein counter events to be acquired are counted in several ranges that can be freely defined in an energy spectrum by a user.

4. The method of claim 3, wherein a separate diffractogram is created for each defined range.

5. The method of claim 1, wherein a mixture ratio of the metals in the X-ray anode is selected such that intensities of measured $K\alpha$ energy lines are equal.

6. The method of claim 1, wherein a mixture ratio of the metals in the X-ray anode is selected such that intensities of measured $K\alpha$ energy lines exhibit a desired intensity ratio.

7. A device for performing the method of claim 1, the device comprising an optical X-ray apparatus suitable for X-ray diffractometry, an energy-dispersive semi-conductor detector and an X-ray anode constructed from a mixed configuration of at least two metals with different characteristic energy lines, wherein said mixed configuration of said at least two metals comprises a sintered powder mixture.

8. The device of claim 7, wherein said mixed configuration of said at least two metals is an alloy.

9. The device of claim 7, wherein said mixed configuration comprises an alternating configuration of strips of at least two pure metals.

10. The device of claim 7, wherein said mixed configuration of said X-ray anode contains Cu and Co.

11. The device of claim 10, wherein said mixed configuration of said X-ray anode also contains Cr and/or Fe.

12. The device of claim 10, wherein said mixed configuration of said X-ray anode also contains molybdenum.

13. The device of claim 11, wherein said mixed configuration of said X-ray anode also contains molybdenum.

14. The device of claim 7, wherein said energy-dispersion semi-conductor detector is a single- or multi-dimensional array detector.

* * * * *